United States Patent [19]

aus der Fünten et al.

[11] 4,211,711
[45] Jul. 8, 1980

[54] METHOD OF PREPARING PHTHALIDE

[75] Inventors: Helmut aus der Fünten, Niederkassel; Wilhelm Vogt, Köln-Ste,uml/u/ lz, both of Fed. Rep. of Germany

[73] Assignee: Dynamit Nobel Aktiengesellschaft, Troisdorf, Fed. Rep. of Germany

[21] Appl. No.: 931,074

[22] Filed: Aug. 4, 1978

[30] Foreign Application Priority Data

Aug. 6, 1977 [DE] Fed. Rep. of Germany ....... 2735600

[51] Int. Cl.$^2$ .......................................... C07D 307/88
[52] U.S. Cl. ............................................ 260/343.3 R
[58] Field of Search ................................ 260/343.3 R

[56] References Cited

U.S. PATENT DOCUMENTS

| | | | |
|---|---|---|---|
| 3,065,237 | 11/1962 | Bortnick et al. | 260/293.79 |
| 4,113,948 | 9/1978 | Aren | 260/343.3 R |

OTHER PUBLICATIONS

Walter Hartung et al., Organic Reactions 7, 263–275, 1953.
Freifelder, Practical Catalytic Hydrogenation Techniques and Applications, p. 537, John Wiley & Sons, N.Y.
Morrison et al., Journ. of the Chem. Soc. London, 1951, p. 952.

*Primary Examiner*—Henry R. Jiles
*Assistant Examiner*—Jane T. Fan
*Attorney, Agent, or Firm*—Sprung, Felfe, Horn, Lynch & Kramer

[57] ABSTRACT

A method has been invented for preparing phthalide by catalytic hydrogenation with a Periodic Table, Group VIII catalyst of a phthalide substituted in the 3-position by a hydroxyl, methoxy or acetoxy group.

6 Claims, No Drawings

METHOD OF PREPARING PHTHALIDE

BACKGROUND

The invention relates to a method of preparing phthalide by the catalytic hydrogenation of phthalides substituted in position 3 with hydroxyl, methoxy or acetoxy groups.

It has already been proposed to transform phthalides substituted with halogen in position 3 to phthalide in the liquid phase at standard pressure or a slight excess pressure, at elevated temperatures and in the presence of a catalyst, such as especially palladium or nickel. For the neutralization of the hydrochloric acid that forms in the reaction, HCl acceptors are added in the reaction (German Patent Application P 26 16 741.9). (corresponding to Ser. No. 783 576).

The hydrochloric acid can also be removed from the reaction mixture with excess hydrogen (German Patent Application P 26 14 294.9). (corresponding to Ser. No. 783 575).

THE INVENTION

It has now been found that phthalide can be prepared in a simple manner by hydrogenation of phthalides substituted in position 3 with hydroxyl, methoxy or acetoxy groups, in a non-aqueous solution, in the presence of conventional hydrogenation catalysts.

In contrast to other methods, the addition of chemicals to control the reaction or bring about neutralization can thus be dispensed with.

Suitable catalysts are the hydrogenation catalysts of Group VIII of the Periodic Table, and therefore especially palladium, platinum, rhodium, nickel and cobalt, and of these, palladium, nickel, cobalt and, in some cases, platinum, can be used to special advantage.

The catalysts that are used are commercial type catalysts which are available to any technician. They can be used either in their metallic form or they can be of the supported type. The catalyst is used in an amount of 0.1 to about 20%, preferably 5 to 15%, of the weight of the substrate.

The temperature generally amounts to from $-10°$ to $150°$ C., preferably $10°$ to $120°$ C.

The pressure can be generally 0.1 to 150 bars, preferably 10 to 120 bars.

Suitable solvents are inert, organic solvents providing sufficient dissolving power for the starting substances and the product. Alcohols, particularly alkanols of 1 to 4 carbon atoms are preferred, especially methanol, and also organic carboxylic acids having 1 to 3 carbon atoms, especially $C_1$-$C_4$ alkane carboxylic acids, such as acetic acid and aliphatic ethers, especially alkyl ethers having up to 6 carbon atoms, such as dimethyl ether, diethyl ether, methyl ethyl ether and di-propyl ether and cyclic ethers, such as tetrahydrofuran, dioxane, etc.

Drying of the solvents is not necessary; in fact, comparatively small amounts of water do no harm.

The formation of phthalide from the above-named compounds takes place in a manner which is unforeseeably specific for the substance, depending on the metal of the catalyst and the reaction parameters. For example, phthalide is obtained in a yield of up to 95% from 3-hydroxyphthalide with a nickel catalyst at especially 50 to 150 bars and 60° to 120° C. On the other hand, 3-acetoxyphthalide can be reduced to phthalide in a high yield under mild conditions, especially 2 to 50 bars and 10° to 60° C., with palladium-containing or, in some cases platinium-containing catalysts, while with nickel catalysts, mixtures of phthalide and o-toluic acid are obtained, depending on the reaction conditions between 10 and 100 bars and 50° to 150° C.

Cobalt was found to be an effective catalyst for the formation of phthalide, from 3-Methoxyphthalid especially at 50 to 150 bars and 60° to 120° C.

The starting substances used for the method of the invention are, in addition to phthalaldehydic acid, the products of the reaction of phthalaladehydic acid with methanol or acetic acid anhydride, which are easy to prepare (J. Org. Chem. 22, 547–55 (1957) and 25, 2020–2022 (1960). In addition, 3-acetoxyphthalide can also be prepared directly by oxidation of o-xylene in the presence of acetic acid anhydride, cf. DT-OS 20 27 039).

The reaction of phthalides substituted in position 3 with hydrogen in the presence of catalysts takes place very rapidly, depending on the substrate used and the catalyst that is present, between $-10°$ and $150°$ C., at pressures of 0.1 to 150 bars. The preferred range when palladium catalysts are used is $10°$ to $60°$ C. and 5 to 30 bars; with nickel and cobalt catalysts it is $60°$ to $120°$ C. and 50 to 150 bars.

It is especially advantageous that the working up of the phthalide can be performed very simply by filtering out the catalyst and removing the solvent. The raw phthalide is already of a high purity of up to 99.2% as determined by gas chromatography. If desired, further purification can be accomplished by distillation or recrystallization. After refinement, the melting point is 72° to 73° C., and the yield is between 90 and 99% of the theory.

The phthalide prepared by the method of the invention is a valuable chemical intermediate for the production of dyes, plant protective agents and pharmaceutical products.

EXAMPLES

EXAMPLE 1

A one-liter lifting magnetic stirrer autoclave is charged with 97.5 g of 3-hydroxyphthalide dissolved in 400 ml of methanol (prepared by dissolving 97.5 g of phthalaldehydic acid in the stated amount of methanol) and 10 g of RCH 55/10 nickel catalyst (commercial product of Hoechst AG). After displacement of the air with nitrogen, hydrogen is forced in so as to produce a pressure of 10 bars, and the temperature is raised, with stirring, to 88° C. The pressure, which is raised to 15 to 17 bars by the heating, is increased to 50 bars by the addition of hydrogen. An absorption of hydrogen immediately takes place, and the absorbed hydrogen is replaced by the continuous injection of hydrogen to maintain the pressure between 45 and 50 bars. To complete the reaction, when the rate of absorption decreases, the reaction is terminated at 90° C. and 70 bars of hydrogen pressure. When the absorption of hydrogen has ended, the batch is cooled, the pressure is let off, the catalyst is filtered out and the solvent is withdrawn. 84.2 g of phthalide remains as residue, with a melting point of 71° C. According to GC analysis, the phthalide content is 97.4% (yield 94.6% of the theory).

EXAMPLE 2

In the manner described in Example 1, the autoclave is filled with 86.4 g of 3-acetoxyphthalide, 400 ml of methanol and 10 g of palladium-on-charcoal catalyst (Pd content 5 wt%), raised to 10 bars with hydrogen, and slowly heated to 35° C. The consumed hydrogen is first replaced by addition in the range up to 10 bars, and then again in the range up to 20 bars and after the reaction rate has decreased. After 3 hours the pressure remains constant. The catalyst is filtered off and the remaining solution is concentrated at 70° C. and 20 Torr in a rotary thin film evaporator. The residue, still smelling slightly of acetic acid, is fractionally distilled between 99° and 103° C. at 0.5 Torr, and the distillate is recrystallized from water. 54 g (90.05% of the theory) of phthalide of a melting point of 72.5° C. is obtained.

EXAMPLE 3

If the procedure of Example 2 is followed, and 10 g of RCH 55/10 nickel catalyst is used instead of palladium catalyst, and if hydrogenation is performed at 30 bars and 80° to 90° C. to saturation, 66 g of a partially crystallizing product is obtained after similar processing. By filtration and pressing on a clay plate, 16 g of substance of a melting point of 78°–82° C. is isolated, which consists, according to infrared analysis, of o-toluic acid contaminated with small amounts of phthalide. Another 5 g of a mixture of o-toluic acid with a slightly higher phthalide content is obtained from the mother liquor. The remaining distillate boils at 0.1 Torr between 80° and 103° C., and GC analysis shows that it consists of 78.2% phthalide and 19.8% 3-acetoxyphthalide. Distillate weight is 40.5 g.

EXAMPLE 4

The autoclave described in Example 1 is filled with 106.6 g of 3-methoxyphthalide, 400 ml of methanol and 15 g of RCH 45/20 cobalt catalyst (commercial product of Hoechst AG). After the addition of hydrogen to a pressure 100 bars, the autoclave is heated at 120° C., the pressure increasing to about 113 bars. After a temperature of 120° C. is reached, the pressure drops to 100 bars and is brought back up to 120 bars by another injection of hydrogen. After 2 hours of reaction at 120° C., the pressure has dropped again to 100 bars; the mixture is cooled, relieved of pressure, and filtered of catalyst. After withdrawal of the solvent, 86.2 g of phthalide (99% of the theory) is obtained having a melting point of 72°–73° C. (GC analysis 99.2% phthalide).

What is claimed is:

1. Method for preparing phthalide, which comprises reacting phthalide substituted in position 3 with hydroxyl, methoxy or acetoxy groups in an inert organic solvent with hydrogen in the presence of a hydrogenation catalyst.

2. Method of claim 1, wherein a metal of Group VIII of the Periodic Table are used as hydrogenation catalyst.

3. Method of claim 1 or 2, wherein the reaction is performed at a temperature of approximately −10° to 150° C.

4. Method of claim 3, wherein the reaction is performed at a temperature of approximately 10° to 120° C.

5. Method of claim 1, wherein the reaction is performed under a pressure of 0.1–150 bars.

6. Method of claim 1, wherein the reaction is performed under a pressure of 10–120 bars.

* * * * *

UNITED STATES PATENT AND TRADEMARK OFFICE
CERTIFICATE OF CORRECTION

PATENT NO. : 4,211,711
DATED : July 8, 1980
INVENTOR(S) : Helmut aus der Fünten et al It is certified that error appears in the above-identified patent and that said Letters Patent are hereby corrected as shown below:

Title Page, Inventors, "Ste, uml/u/lz" should be "Sülz".

Signed and Sealed this

Eleventh Day of November 1980

[SEAL]

Attest:

SIDNEY A. DIAMOND

Attesting Officer  Commissioner of Patents and Trademark